United States Patent [19]
Lindstrom et al.

[11] Patent Number: 5,175,310
[45] Date of Patent: Dec. 29, 1992

[54] PROCESS FOR PRODUCING ALKYLTHIO- AND ARYLTHIO-SUBSTITUTED CARBOXYLIC ACIDS AND THEIR THIOESTERS

[75] Inventors: Michael J. Lindstrom, Downingtown; Bernard Buchholz, Whitpain; Robert B. Hager, Collegeville, all of Pa.

[73] Assignee: Elf Atochem North America, Inc., Philadelphia, Pa.

[21] Appl. No.: 494,715

[22] Filed: Mar. 16, 1990

[51] Int. Cl.$^5$ ............................................. C07D 333/00
[52] U.S. Cl. .................................. 549/273; 549/295; 558/252; 562/512
[58] Field of Search ............... 549/295, 273; 558/252; 562/512

[56] References Cited

U.S. PATENT DOCUMENTS

| | | | |
|---|---|---|---|
| 2,842,587 | 7/1958 | Wagner | 549/63 |
| 2,842,590 | 7/1958 | Wagner | 549/63 |
| 2,872,458 | 2/1959 | Wagner | 252/94 |
| 4,311,849 | 4/1982 | Ziman | 549/63 |
| 4,758,369 | 7/1988 | Dyroff et al. | 549/91 |

FOREIGN PATENT DOCUMENTS 0651165  3/1951  United Kingdom.

OTHER PUBLICATIONS

Chem. Ber., 83, pp. 265–268 (1950).
Tet. Letters, p. 4369 (1977).
Tet. Letters, p. 4361 (1977).
Chem. Ber., 94, p. 2060 (1961).
Tet. Letters p. 3859 (1977). Kelly et al., "Lithium Thiomethoxide: A Convenient Mercaptide Reagent".
J. Organometal. Chem., 25, p. 33 (1970).
Node et al., J. Org. Chem., 45, p. 4275 (1980).
Node et al. J. Org. Chem., 46, p. 5163 (1981).
Node et al. Tet. Letters, 52, p. 5211 (1978).
J. Org. Chem., 39, p. 2648 (1974).
Chemical Processing, Feb. 1987.
Canadian Journal of Chemistry, 33, pp. 679–682 (1955).

Primary Examiner—Marianne M. Cintus
Assistant Examiner—Catherine Scalzo
Attorney, Agent, or Firm—Panitch Schwarze Jacobs & Nadel

[57] ABSTRACT

A process is provided for producing alkylthio-substituted carboxylic acids and arylthio-substituted carboxylic acids and their corresponding alkylthio-substituted thioesters and arylthio-substituted thioesters. The process comprises reacting a mercaptan with a lactone in the presence of an acidic catalyst at temperatures of about 100° C. to about 350° C. The process for preparing the thio-substituted carboxylic acids and thio-substituted thioesters may be a continuous process or a batch process.

27 Claims, 3 Drawing Sheets

PROCESS FOR PRODUCING ALKYLTHIO- AND ARYLTHIO-SUBSTITUTED CARBOXYLIC ACIDS AND THEIR THIOESTERS

BACKGROUND OF THE INVENTION

1. Field of the Invention

This invention relates to a process for preparing alkylthio- and arylthio-substituted carboxylic acids and their corresponding thioesters, comprising reacting a mercaptan with a lactone in the presence of an acidic catalyst. In the preferred embodiments of the present invention, the process provides continuous production and batch production of thio-substituted carboxylic acids and the corresponding thio-substituted thioester.

2. Description of the Prior Art

Alkylthio-substituted carboxylic acids and arylthio-substituted carboxylic acids (hereinafter sometime jointly referred to by the phrase "alkyl- and arylthio-substituted carboxylic acids") are important synthetic intermediates for a wide range of product applications. For example, methionine (2-amino-4-methylthiobutyric acid) and its hydroxy analog, 2-hydroxy-4-methylthiobutyric acid, are widely used as animal-feed supplements. In addition, sulfone peroxycarboxylic acids have been reported as a novel class of stable, solid, bleach materials for detergent applications, as disclosed in U.S. Pat. No. 4,758,369.

The reaction of lactones, for example, γ-butyrolactone, with various alkyl metal mercaptans and aryl metal mercaptans (i.e., mercaptide ions), typically conducted in the presence of a co-solvent, for example dimethylformamide (DMF), dimethylsulfoxide (DMSO) and hexamethylphosphoramide (HMPA), to facilitate solubilizing the mercaptide ion, is well known in the literature. Typical mercaptides comprise sodium and potassium metal. The cleavage of α-aminobutyrolactone with sodium methyl mercaptide, followed by acidification of the resulting sodium carboxylate to produce methionine or its derivatives, is described in several references, for example, *Chem. Ber.*, 83, pp. 265-268 (1950); U.S. Pat. No. 4,311,849 and British Patent Application 651,165 (*Chem. Abst.* 51:2853c). In addition, other ring opening reactions of various lactones with mercaptide ions or metal salts of selenium compounds (i.e., selenide ions) have been reported, for example, U.S. Pat. Nos. 2,842,587; 2,842,590 and 2,872,458; *Tet. Letters*, p. 4369 (1977); *Tet. Letters*, p. 4361 (1977); *Chem. Ber.* 94, p. 2060 (1961); *Tet Letters*, p. 3859 1977; *J. Organometal. Chem.*, 25, p. 33 (1970).

Preparation of the mercaptide ion typically comprises reacting the mercaptan with a metal hydride, for example, sodium hydride (NaH), potassium hydride (KH) or lithium hydride (LiH). Alternatively, the metal mercaptan may be prepared by reacting the mercaptan with a metal, for example, potassium metal (K) or lithium metal (Li). The use of metal hydrides, for example, NaH, is well known to those skilled in the art of organic synthetic chemistry. However, the use of metal hydrides often proves to be problematic due to their flammability and moisture sensitivity. Such drawbacks often require maintaining the metal hydride under an inert atmosphere during handling, as well as maintaining an inert atmosphere over the reaction medium. Similarly, metals, such as K, are difficult to handle since they are flammable and moisture sensitive. Therefore, the present invention substantially eliminates the need to use mercaptide ions to prepare thio-substituted carboxylic acids and thio-substituted thioesters from lactones.

Several papers report the use of Lewis acid complexing agents, for example, aluminum chloride, to facilitate carbon-oxygen bond cleavage in esters and lactones. See, for example, *J. Org. Chem.*, 45, p. 4275 (1980); *J. Org. Chem.*, 46, p. 5163 (1981) and *Tet. Letters*, 52, p. 5211 (1978). In all of these cases, the Lewis acid is used in stoichiometric amounts. While the use of Lewis acid complexing agents, such as aluminum chloride, is not as problematic as the use of metal hydrides and metals when preparing metal mercaptans, they are generally moisture sensitive and corrosive. The present invention substantially eliminates the need for such Lewis acid complexing agents when reacting mercaptans with lactones.

Moreover, although free mercaptans are known to ring-open highly strained lactones, for example, propiolactone (*J. Org. Chem.*, 39, p. 2648 (1974)), there appear to be no examples in the literature of similar reactions of higher lactones, for example, butyrolactone and valerolactone. The present invention provides a method for ring-opening such higher lactones with free mercaptans.

SUMMARY OF THE INVENTION

One aspect of the present invention is a process for producing a thio-substituted carboxylic acid selected from the group consisting of an alkylthio-substituted carboxylic acid and an arylthio-substituted carboxylic acid comprising reacting in the presence of an acidic catalyst a lactone selected from the group consisting of an alkyl lactone and an aryl lactone and a mercaptan selected from the group consisting of an alkyl mercaptan and an aryl mercaptan, where the lactone to mercaptan mole ratio is about 5:1 to about 15:1, at a temperature of about 100° C. to about 350° C.

Another aspect of the present invention is a process for producing a thio-substituted thioester selected from the group consisting of an alkylthio-substituted thioester and an arylthio-substituted thioester comprising reacting in the presence of an acidic catalyst a lactone selected from the group consisting of an alkyl lactone and an aryl lactone and a mercaptan selected from the group consisting of an alkyl mercaptan and an aryl mercaptan, where the lactone to mercaptan mole ratio is about 0.1:1 to about 2:1, at a temperature of about 100° C. to about 350° C.

Yet another aspect of the present invention is a process for preparing a compound having a formula by reacting in the presence of an acidic catalyst at a temperature of about 100° C. to about 350° C. a mercaptan having a formula RSH with a lactone having a formula wherein R is a radical selected from the group consisting of substituted or unsubstituted alkyl of 1 to 25 carbons, substituted or unsubstituted cycloalkyl of 5 to 25 carbons, substituted or unsubstituted aryl of 6 to 25 carbons, substituted or unsubstituted aralkyl of 7 to 26 carbons, substituted or unsubstituted alkyl hydroxy of 1 to 25 carbons, substituted or unsubstituted alkoxy alkyl of 2 to 25 carbons, halogen-substituted aliphatic of 1 to 25 carbons, benzothiazol-2-yl and pyridin-4-yl, where the substituents for R are hydroxy, halogen, alkyl of 1 to 6 carbons or aryl of 6 to 12 carbons;

A is selected from the group consisting of $-YCR^1R^2(CR^3R^4)_x-$ and wherein

Y is the bond location to the carbonyl carbon;

$R^1$, $R^2$, $R^3$ and $R^4$ are independently selected from the group consisting of hydrogen, halogen, substituted or unsubstituted alkyl of 1 to 25 carbons, substituted or unsubstituted aryl of 6 to 25 carbons, substituted or unsubstituted aralkyl of 7 to 26 carbons, substituted or unsubstituted alkoxy alkyl of 2 to 25 carbons, halogen-substituted alkyl of 1 to 25 carbons, substituted or unsubstituted alkoxy of 2 to 25 carbons, substituted or unsubstituted thioalkoxy of 1 to 25 carbons, dialkylamino of 2 to 25 carbons and diarylamino of 12 to 25 carbons, where the substituents for any of $R^1$, $R^2$, $R^3$ and $R^4$ are hydroxy, halogen, alkyl of 1 to 6 carbons or aryl of 6 to 12 carbons;

$R^1$ and $R^3$ may together comprise a ring and $R^2$ and $R^4$ may together comprise a ring;

$R^5$, $R^6$, $R^7$, $R^8$, $R^9$ and $R^{10}$ are independently selected from the group consisting of hydrogen, halogen, substituted or unsubstituted alkyl of 1 to 25 carbons, substituted or unsubstituted aryl of 6 to 25 carbons, substituted or unsubstituted aralkyl of 7 to 26 carbons, substituted or unsubstituted alkoxy alkyl of 2 to 25 carbons, halogen-substituted alkyl of 1 to 25 carbons, substituted or unsubstituted alkoxy of 1 to 25 carbons, substituted or unsubstituted thioalkoxy of 1 to 25 carbons, dialkylamino of 2 to 25 carbons and diarylamino of 12 to 25 carbons, where the substituents for any of $R^5$, $R^6$, $R^7$, $R^8$, $R^9$ and $R^{10}$ are hydroxy, halogen, alkyl of 1 to 6 carbons or aryl of 6 to 12 carbons;

x is an integer from 2 to 5;

y is an integer from 1 to 5; and

Z is selected from the group consisting of —OH and —SR.

BRIEF DESCRIPTION OF THE DRAWINGS

For the purpose of illustrating the invention, there is shown in the drawings forms which are presently preferred; it being understood, however, that this invention is not limited to the precise arrangements and instrumentalities shown.

DETAILED DESCRIPTION OF THE PREFERRED EMBODIMENTS

In accordance with the present invention, it has been discovered that mercaptans react with lactones in the presence of an acid catalyst, to form the open chain thio-substituted carboxylic acids and the corresponding thio-substituted thioesters. The process of this invention is an improvement over the prior art, since it eliminates the need for a co-solvent, for example, dimethylformamide (DMF), dimethylsulfoxide (DMSO) and hexamethylphosphoramide (HMPA). Moreover, the present invention allows utilization of free mercaptans as opposed to their corresponding mercaptide ions. In addition, the desired thio-substituted carboxylic acid is obtained directly rather than via the metal carboxylate intermediate which requires acidification to generate the free carboxylic acid. The formed thio-substituted carboxylic acid can be converted, in situ, to the corresponding thio-substituted thioester by controlling the stoichiometry of the reactants. High lactone to mercaptan mole ratios favor formation of the thio-substituted carboxylic acid as the major product, whereas low ratios of lactone to mercaptan favor formation of the thio-substituted thioester.

As indicated in the above Summary of the Invention, the present invention comprises a process for preparing a compound having a formula by reacting in the presence of an acidic catalyst at a temperature of about 100° C. to about 350° C. a mercaptan having a formula RSH with a lactone having a formula wherein A is selected from the group consisting of $-YCR^1R^2(CR^3R^4)_x-$ and and R, $R^1$, $R^2$, $R^3$, $R^4$, $R^5$, $R^6$, $R^7$, $R^8$, $R^9$, $R^{10}$, Y, Z, x and y are as previously defined. Likewise, the substituents for the substituted R, $R^1$, $R^2$, $R^3$, $R^4$, $R^5$, $R^6$, $R^7$, $R^8$, $R^9$ and $R^{10}$ groups, even in the following preferred and more preferred embodiments, are as previously defined.

Preferably, A is $-YCR^1R^2(CR^3R^4)_x-$.

Preferably, R is substituted or unsubstituted alkyl of 1 to 10 carbons or substituted or unsubstituted aryl of 6 to 10 carbons. More preferably, R is substituted or unsubstituted alkyl of 1 to 10 carbons. Even more preferably, R is n-octyl.

Preferably, $R^1$, $R^2$, $R^3$ and $R^4$ are independently selected from the group consisting of hydrogen and substituted or unsubstituted alkyl of 1 to 10 carbons. More preferably, $R^1$, $R^2$, $R^3$ and $R^4$ are independently hydrogen.

Preferably, $R^5$, $R^6$, $R^7$, $R^8$, $R^9$ and $R^{10}$ are independently selected from the group consisting of hydrogen and substituted or unsubstituted alkyl of 1 to 10 carbons.

Preferably, Z is selected from the group consisting of hydroxy and n-octyl mercaptyl.

Preferably, x is 2.

In addition, the reaction of the present invention may be set forth in the following exemplary general equation for an alkylthio-substituted carboxylic acid and an alkylthio-substituted thioester:

where

R and x are as previously defined.

For this exemplary reaction, $R^1$, $R^2$, $R^3$ and $R^4$ each is hydrogen. As would be apparent to those of ordinary skill in the art, the reaction equation can be rewritten for any of the previously indicated alternative embodiments.

The reaction of the present invention proceeds in accordance with various reaction parameters. The reaction parameters and conditions will be set forth below with reference to the reactor systems schematically illustrated in the drawings.

Figure 1:
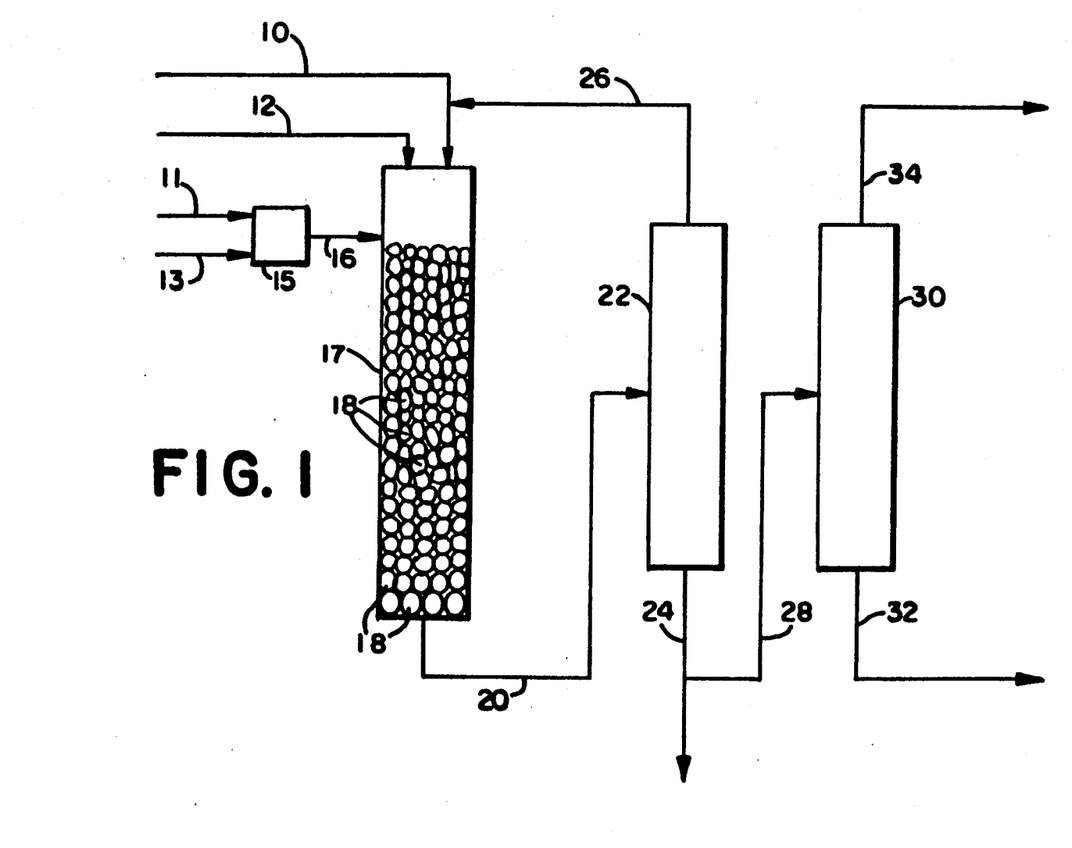
FIG. 1 is a schematic representation of a reactor system for preparing the thio-substituted carboxylic acids and thio-substituted thioesters in accordance with the present invention.

Referring to the drawings wherein like numerals refer to like elements throughout the several views, FIG. 1 is a schematic representation of a reactor system for use in practicing the invention. The starting mercaptan and starting lactone may be fed separately or as a mixture into a reactor. Thus, the mercaptan may be added through a conduit 10 and the lactone via a conduit 12 into a reactor 17. Alternatively, the mercaptan and lactone may be fed into a mixing apparatus 15 via conduits 11 and 13, respectively. After the mercaptan and lactone are mixed, the mixture is fed into the reactor 17 via a conduit 16. The starting mercaptan and lactone are preferably liquids, to facilitate their flow into the reactor 17 via the conduits 10 and 12 or the conduit 16. If either the starting mercaptan or lactone is a solid, the solid may be dissolved in an inert solvent, for example, benzene, toluene and hexane, prior to feeding the starting mercaptan and lactone into the reactor 17. Alternatively, if the starting mercaptan or lactone is a solid, the solid may be liquified by heating the solid to the melting point prior to feeding the starting mercaptan and lactone into the reactor 17.

The reactor 17 is a vertical, fixed-bed reactor which comprises heating means to heat the reactor contents. The reactor is charged, prior to introducing the mercaptan and lactone, with at least one catalyst 18. Suitable catalysts for the practice of the present invention are generally acidic catalysts, for example, LZ-Y62 and LZ-Y82 Zeolites (products of Union Carbide), Silicalites ®, such as Union Carbide's SR-115 and S-115, silica, silica-aluminas, such as LA-MZ-3P (product of Akzo), naturally occurring zeolites such as mordenites, and non-oxidizing acids like methane-sulfonic acid (MSA). However, if MSA is used as a catalyst in a fixed-bed reactor, it must be adsorbed or imbibed on an inert support or on one of the aforementioned solid catalysts. Catalysts which are normally inactive, such as Union Carbide's LZ-Y52 and various aluminas may be activated by treatment with non-oxidizing acids, for example, MSA. Catalysts which are normally considered basic in nature are not suitable for this invention, for example, magnesias, zirconias, titanias and amines.

The temperature of the reaction can range from about 100° C. to about 350° C., depending upon the respective reactivities and boiling points of the starting lactone and mercaptan and their residence time in the reactor. One measure of reactor residence time is referred to as mole velocity, which is defined as gram-moles of reactant fed per kilogram of catalyst per 24-hour day. Alternatively, the mole velocity may be defined equivalently as pound-moles per 1000-pounds catalyst per 24-hour day. The optimum mole velocity depends, in turn, on the temperature of the reactor. At lower temperatures (about 150° C. to about 250° C.), mole velocities between 50 and 100 are most preferred, while at higher temperatures (about 250° C. to about 350° C.) mole velocities between 100 and 300 are most preferred.

As the mixture of the mercaptan and lactone contact the hot catalyst bed 18 contained in the reactor 17, the ring-opening reaction occurs to form the corresponding carboxylic acid which, depending upon the mole ratio of the reactants, can react with additional mercaptan to form the corresponding thioester. High mole ratios of lactone to mercaptan (about 5:1 to about 15:1 and preferably about 10:1) favor almost exclusive formation of the acid, while advantageously equal (1:1) or low mole ratios (about 0.1:1 to about 2:1, and preferably about 0.5:1) result in mixtures of acid and thioester. After the reaction mixture has remained in the reactor for the desired residence time, the reaction mixture or reactor effluent is fed via a conduit 20 into a distillation column 22 which comprises packing material or trays, heating means and vacuum means, to heat and depressurize the contents of the distillation column 22. The operating temperature and pressure of the distillation column 22 are dictated by the boiling points of the starting mercaptan, starting lactone, thio-substituted carboxylic acid and thio-substituted thioester. Distillation temperatures between about 50° C. and about 250° C. and pressures from about 5 millimeters (mm) of mercury (Hg) to about atmospheric pressure (760 mm of Hg) are typical.

If the reaction of the mercaptan and lactone to form the thio-substituted carboxylic acid and thio-substituted thioester, which primarily takes place in the reactor 17 is incomplete, the reactor effluent comprises thio-substituted carboxylic acid, thio-substituted thioester, unreacted mercaptan and unreacted lactone, as it is fed into the distillation column 22. The unreacted lactone and mercaptan, generally having lower boiling points and heats of vaporization than the thio-substituted carboxylic acid and thio-substituted thioester, are preferentially distilled from the distillation column 22 and recycled back into the reactor 17 via a conduit 26. The recycled lactone and mercaptan are then further heated in the reactor 17 to undergo the ring-opening reaction. The reactor effluent from the recycled material, as described previously, is fed via the conduit 20 into the distillation column 22. This recycling process continues until substantially all of the starting lactone and mercaptan are converted to the thio-substituted carboxylic acid and thio-substituted thioester.

At this point in the process, the reaction mixture contained in the distillation column 22 substantially comprises the thio-substituted carboxylic acid and the thio-substituted thioester. The reaction mixture may be drained from the distillation column 22 via a conduit 24 and collected. Alternatively, the reaction mixture may be fed via a conduit 28 into a second distillation column 30. As in the distillation column 22, the temperature of the distillation column 30 is typically between about 50° C. and about 250° C. and the pressure is from about 5 mm to about 760 mm of Hg. Final separation of the thio-substituted carboxylic acid and thio-substituted thioester is accomplished via distillation in the distillation column 30. The thio-substituted thioester, generally being more non-polar than the corresponding thio-substituted carboxylic acid, generally has a lower boiling point. As a result, the thio-substituted thioester generally preferentially refluxes and distills to the top of the distillation column 30, and is removed via a conduit 34. Conversely, the thio-substituted carboxylic acid, generally having a higher boiling point than the corresponding thio-substituted thioester, does not boil and substantially remains in the bottom of the distillation column 30, and may be removed and collected via a conduit 32. In addition, water formed during the thioesterification process may be removed by distillation from the reaction mixture during the final distillation process in the distillation column 30 or alternatively, reactor effluent which is optionally collected from the distillation column 22 via the conduit 24 may be subsequently distilled to remove water, or the water may be physically removed via a decanter or similar separation device.

Figure 2:
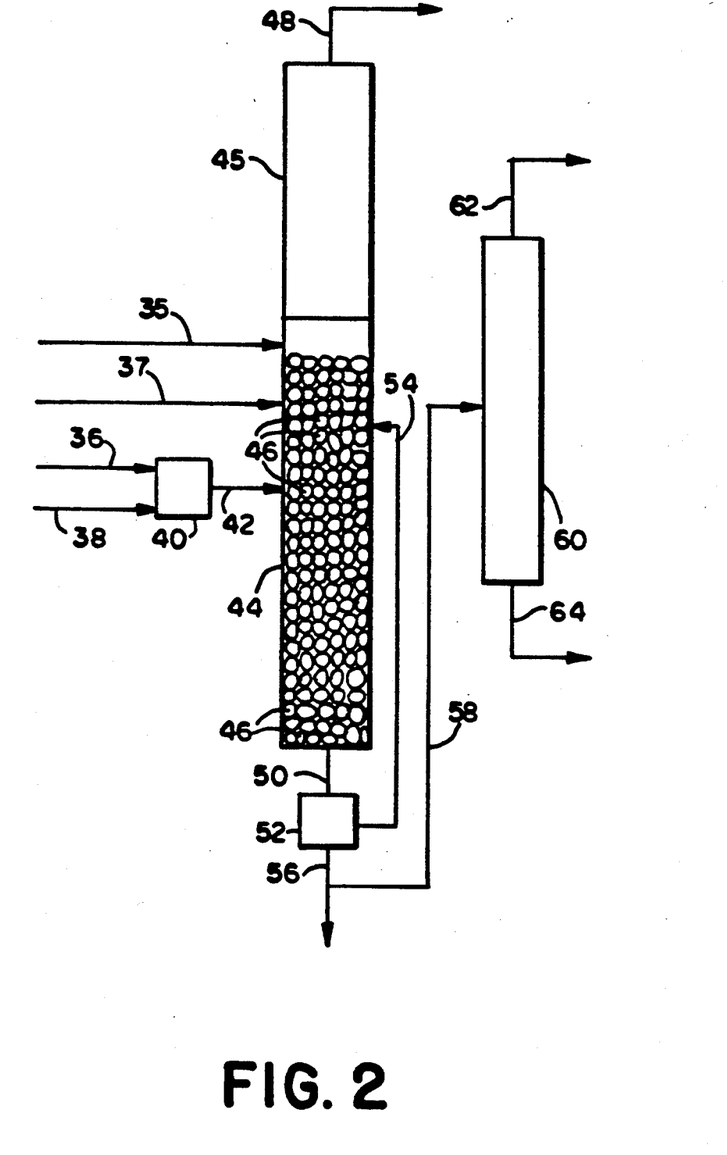
FIG. 2 is a schematic representation of a reactor system for preparing the thio-substituted carboxylic acids and thio-substituted thioesters in accordance with another embodiment of the invention.

A schematic representation of a reactor system in accordance with another embodiment of the present invention is depicted in FIG. 2. This processing apparatus is designed to combine the chemical reaction of the starting mercaptan and lactone with product separation in a discrete unit operation. This concept, referred to as "Catalytic Distillation," is utilized for several commercial processes. See W. Stadig, "Catalytic Distillation: Combining Chemical Reaction with Product Separation," *Chemical Processing*, February, 1987. The advantage of this configuration is that the thio-substituted carboxylic acid product is substantially removed from the reaction zone as it is formed, if desired, thereby minimizing formation of the thio-substituted thioester.

As in the previous embodiment, the starting mercaptan and lactone may be introduced separately into a reactor 44 by feeding the mercaptan via a conduit 35 and the lactone via a conduit 37 into the reactor 44. Alternatively, the mercaptan and lactone may be fed via conduits 36 and 38, respectively, into a mixing apparatus 40, where the two components are mixed. The mixture is subsequently fed through conduit 42 into the reactor 44. As in the previous embodiment, the starting mercaptan and lactone are preferably liquids. If solids, they may be dissolved in an inert solvent or liquified by heating to their melting points prior to entering the reactor 44.

Within the reactor 44, fitted with a reflux column 45, the starting mercaptan and starting lactone may be heated to a desired temperature by reactor heating means and subjected to a desired pressure by reactor vacuum means to vaporize the starting mercaptan and starting lactone. Desirable temperatures and pressures are, for example, between about 50° C. and about 250° C. and from about 5 mm of Hg to about atmospheric pressure.

Prior to introducing the mercaptan and lactone, the reactor 44 is charged with packed, trayed or bundled catalyst 46 of the type described with reference to the first embodiment illustrated in FIG. 1. After the mercaptan and lactone are heated and preferably subjected to a vacuum in reactor 44, the starting materials vaporize and react to form the thio-substituted carboxylic acid and thio-substituted thioester. Due to the generally lower boiling points and heats of vaporization of the starting lactone and mercaptan as compared to the thio-substituted carboxylic acids and thio-substituted thioesters, the unreacted starting materials generally distill into the reflux column 45. As the unreacted starting materials are refluxed, they react and the thio-substituted carboxylic acid and thio-substituted thioester condense and flow down, out of the reaction zone. Hence, this configuration is intended to minimize the formation of the thio-substituted thioester, since the thio-substituted carboxylic acid product is removed from the reaction zone, away from thioester forming mercaptan, substantially as it is formed. Any water resulting from formation of the thio-substituted thioester is distilled to the top of the reflux column 45 and may be removed from the system via a conduit 48.

The reaction mixture or reactor effluent, comprising the thio-substituted carboxylic acid and thio-substituted thioester, as well as minimal amounts of unreacted mercaptan and lactone, is fed via a conduit 50 into a flash pot 52. The mixture then undergoes flash distillation wherein unreacted mercaptan and lactone recycle back into the reactor 44 via a conduit 54. The unreacted mercaptan and lactone are then subjected to temperatures and pressures to give the thio-substituted carboxylic acid and the thio-substituted thioester products, as described hereinbefore. This recycling process continues until the mercaptan and lactone are substantially fully reacted, at which time the reactor effluent, comprising acid and thioester products may be removed from the system and collected via a conduit 56.

Alternatively, the product mixture may be fed via a conduit 58 into a distillation tower 60. The distillation tower contains an appropriate packing, such that upon subjecting the product mixture to a desired temperature at a desired pressure, the thio-substituted carboxylic acid and the thio-substituted thioester products may be separated by distillation, as described hereinbefore for FIG. 1. The two products are then removed from the distillation tower 60 via separate conduits, for example, the thio-substituted carboxylic acid via a conduit 64 and the thio-substituted thioester via a conduit 62.

Figure 3:
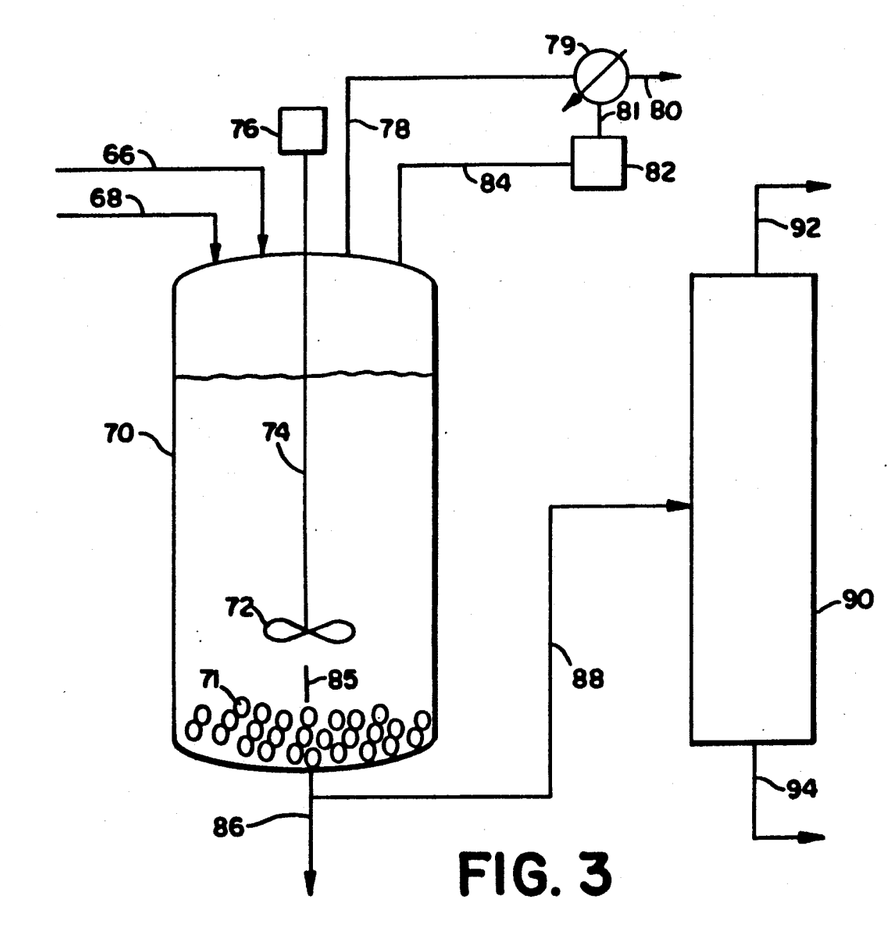
FIG. 3 is a schematic representation of a reactor system for preparing the thio-substituted carboxylic acids and thio-substituted thioesters according to another alternate embodiment of the present invention.

A schematic representation of a reactor designed for batch production in accordance with another embodiment of the present invention is depicted in FIG. 3. The starting mercaptan is fed via a conduit 66 and the starting lactone is fed via a conduit 68 into a continuously stirred tank reactor (CSTR) 70 or similar pressure vessel which contains a catalyst charge 71. As described hereinbefore, the starting mercaptan and lactone are preferably liquids and the mole ratio of the reactants used depends upon the desired product composition. High lactone to mercaptan mole ratios favor formation of the thio-substituted carboxylic acid as the major product, whereas low ratios of lactone to mercaptan favor formation of the thio-subsituted thioester. Temperatures within the reactor 70 can range between about 150° C. and about 350° C., while the preferred temperature range is about 150° C. to about 250° C. The most preferred temperature range is about 190° C. to about 250° C.

The reactor 70 is charged with the catalyst 71, either before or after introducing the mercaptan and lactone, but prior to heating and pressurizing the reactor 70. The amount of catalyst introduced into the reactor 70 can range from about 0.1% by weight to about 50% by weight based upon the amount of starting mercaptan or lactone introduced into the reactor 70. About 10% by weight of catalyst charged into the reactor, based upon the amount of mercaptan and lactone introduced into the reactor, is most preferred. In addition, the catalyst is preferably in the form of a powder. This will increase the surface area of the catalyst and improve its dispersibility throughout the reaction medium, thereby improving its catalytic efficiency.

After the mercaptan, lactone and catalyst are introduced into reactor 70 and preferably prior to heating and pressurizing the reactor, the reaction medium is agitated. In the presently preferred embodiment, this agitation is provided by stirring blades 72 which are connected to a motor 76 by a shaft 74. Preferably, the reaction mixture is sufficiently agitated such that the mercaptan and lactone are homogeneously mixed, and the catalyst is equally dispersed throughout the reaction medium.

After the mercaptan, lactone and catalyst are charged into the reactor 70 and the reaction mixture is agitated, the reactor is heated and pressurized. The reaction can be conducted at about atmospheric pressure or superatmospheric pressure depending upon the reaction temperatures and vapor pressures of the reactants. Reaction pressures in the range of about 10 pounds per square inch guage (psig) to about 15 psig are preferred.

The reaction may be monitored by removing aliquots of the reaction mixture, filtering the aliquots to remove catalyst and analyzing the filtered aliquots by gas chromotography. The reaction progress can be determined by the disappearance of peaks corresponding to starting mercaptan and lactone, or by the appearance of peaks corresponding to thio-substituted carboxylic acid and thio-substituted thioester in the gas chromatogram. The analysis of the reaction mixture will not be further discussed here, as it involves techniques well known to those skilled in the art.

As the reaction proceeds, the generally lower boiling mercaptan and lactone boil and distill into a conduit 78, and condense within a reflux accumulator 79. The condensed mercaptan and lactone may be removed from the system via a conduit 80, or alternatively may pass via a conduit 81 into a storage container 82. The collected mercaptan and lactone may then be recycled into the reactor 70 via a conduit 84. The recycled mercaptan and lactone are then subjected to temperatures and pressures to react to give the thio-substituted carboxylic acid and thio-substituted thioester. This recycling process may continue until the starting mercaptan and lactone are substantially completely consumed or the desired product ratio of thio-substituted carboxylic acid to thio-substituted thioester is obtained.

The reactor 70 is then depressurized to atmospheric pressure, and preferably to a reduced pressure of about 1 mm of Hg to about 50 mm of Hg. The water formed during the thioesterification process, unreacted mercaptan and unreacted lactone may be removed from the reactor 70 by distillation via the conduit 78 into the reflux accumulator 79. The water, mercaptan and lactone may then be removed from the system via the conduit 80. It is most convenient to remove the water and unreacted starting materials at reduced pressure, since less heat is required to heat the water, mercaptan and lactone to their boiling points for distillation.

The crude product mixture, comprising thio-sustituted carboxylic acid and thio-substituted thioester can be removed from the reactor via a dip-tube 85 and conduit 86. After filtering to remove catalyst 71, the crude product mixture may be used for other synthetic or commercial processes, stored for later use or further purified. Alternatively, the crude reaction mixture may be removed from the reactor 70 and fed via a conduit 88 into a distillation column 90. Within the distillation column 90, the crude reaction mixture is subjected to sufficient temperature and pressure, as described hereinbefore, to separate the thio-substituted carboxylic acid and thio-substituted thioester via distillation. For example, the thio-substituted carboxylic acid is separated and removed from the crude reaction mixture via a conduit 94, and the thio-substituted thioester is removed via a conduit 92. In general, the thio-substituted carboxylic acid, as the higher boiling product, is removed through the lower conduit 94 of the distillation column and the thio-substituted thioester, as the lower boiling product, is removed through the upper conduit 92 of the distillation column 90.

The time required for the starting mercaptan and lactone to be consumed or the time required to obtain the desired ratio of thio-substituted carboxylic acid to thio-substituted thioester can vary greatly, depending upon the reaction conditions and the exact starting mercaptan and lactone utilized. However, reaction times of between about 4 hours and about 25 hours are typical.

After the crude reaction products are removed from the reactor 70 via the dip-tube 85 and the conduit 86 or optionally fed via the conduit 88 into the distillation column 90, the reactor 70 may be charged with additional mercaptan and lactone. In this manner, the present embodiment provides a batch production process for preparing thio-substituted carboxylic acids and thio-substituted thioesters.

The present invention will now be illustrated in more detail by reference to the following specific, non-limiting examples.

EXAMPLE 1

Batch screening of various catalysts

γ-Butyrolactone (5.0 g, 0.058 mole) and n-octyl mercaptan (8.5 g, 0.058 mole) were each introduced into ten separate 200 mL round-bottom flasks. Each flask was charged with 2 g of a separate catalyst. The mixtures were stirred and heated at 190° C. to 200° C. for 4 hours and subsequently analyzed by gas chromotography. The results of these screening experiments, which were designed to analyze the effectiveness of different catalysts, are presented in Table 1 below. The resulting products from the reaction are 4-(n-octylthio)butyric acid (4-OTBA), n-octylthio-4-(noctylthio)butyrate (thioester), di-n-octyl sulfide (DOS) and di-n-octyl disulfide (DOD). Table 1 reflects area percentages of the individual components; the remaining percentage is unreacted starting mercaptan and starting lactone.

TABLE 1

| Catalyst | 4-OTBA | DOS | DOD | Thioester |
|---|---|---|---|---|
| LZ-Y52 | —* | — | — | — |
| LZ-Y62 | 1.2 | 0.3 | 0.4 | 0.4 |
| LZ-Y82 | 6.3 | 0.9 | 0.4 | 4.7 |
| Silicalite | 25.0 | 0.0 | 0.1 | 10.3 |
| Silica/Alumina | 9.7 | 2.6 | 0.3 | 20.5 |
| F-1 Alumina | — | — | — | — |
| Anhydrous MSA | 20.5 | 10.2 | 0.1 | 29.0 |
| MgO | — | — | — | — |
| Titania | — | — | — | — |
| Zirconia | — | — | — | — |

*— indicates no reaction

EXAMPLE 2

Continuous preparation of 4-OTBA and the corresponding thioester

An equimolar mixture of γ-butyrolactone and n-octyl mercaptan was fed into a stainless steel fixed-bed reactor (length is 12 in., I.D. is 1 in.) containing 75 g of Union Carbide's S-115 Silicalite (1/16 inch extrudites). The reactor was maintained at 200° C. via oven heating. Approximately 0.6 g of the mixture (mole velocity of about 50) was fed into the reactor per minute. The reactor effluent was collected in a round-bottom flask which was fitted with an upper reflux condenser and a lower stop-cock. The reflux condenser trapped any refluxing reaction mixture. In a typical run, a desired amount of reactor effluent was collected in the flask, the closed stop-cock was opened and the reactor effluent was removed from the flask and collected in a separate receiver. The collected product was analyzed by gas chromatography to quantitate the amounts of starting mercaptan, starting lactone, thio-substituted carboxylic acid and thio-substituted thioester present. 72 g of the lactone-mercaptan mixture was fed into the reactor over a 2-hour period. The effluent (67.5 g) produced the following gas chromatographic analysis (area %): 27.5% 4-OTBA, 15.8% thioester and the remainder as unreacted mercaptan and lactone. This corresponds to an approximate conversion of lactone to thio-substituted carboxylic acid and thio-substituted thioester of 62.3% with a 73% yield of 4-OTBA.

The present invention may be embodied in other specific forms without departing from the spirit or essential attributes thereof and, accordingly, reference should be made to the appended claims, rather than to the foregoing specification as indicating the scope of the invention.

We claim:

1. A process for producing a thio-substituted carboxylic acid selected from the group consisting of an alkylthio-substituted carboxylic acid and an arylthio-substituted carboxylic acid comprising reacting in the presence of a catalytic amount of an acidic catalyst a lactone selected from the group consisting of an alkyl lactone and an aryl lactone and a mercaptan selected from the group consisting of an alkyl mercaptan and an aryl mercaptan, where the lactone to mercaptan mole ratio is about 5:1 to about 15:1, at a temperature of about 100° C. to about 350° C.

2. The process of claim 1 wherein the mole ratio process of lactone to mercaptan is about 10:1.

3. A process for producing a thio-substituted thioester selected from the group consisting of an alkylthio-substituted thioester and an arylthio-substituted thioester comprising reacting in the presence of a catalytic amount of an acidic catalyst a lactone selected from the group consisting of an alkyl lactone and an aryl lactone and a mercaptan selected from the group consisting of an alkyl mercaptan and an aryl mercaptan, where the lactone to mercaptan mole ratio is about 0.1:1 to about 2:1, at a temperature of about 100° C. to about 350° C.

4. The process of claim 3 wherein the mole ratio of lactone to mercaptan is about 0.5:1.

5. A process for preparing a compound having a formula by reacting in the presence of a catalytic amount of an acidic catalyst at a temperature of about 100° C. to about 350° C. a mercaptan having a formula RSH with a lactone having a formula wherein R is a radical selected from the group consisting of substituted or unsubstituted alkyl of 1 to 25 carbons, substituted or unsubstituted cycloalkyl of 5 to 25 carbons, substituted or unsubstituted aryl of 6 to 25 carbons, substituted or unsubstituted aralkyl of 7 to 26 carbons, substituted or unsubstituted alkyl hydroxy of 1 to 25 carbons, substituted or unsubstituted alkoxy alkyl of 2 to 25 carbons, halogen-substituted aliphatic of 1 to 25 carbons, where the substituents for R are hydroxy, halogen, alkyl of 1 to 6 carbons or aryl of 6 to 12 carbons;

A is selected from the group consisting of —YCR$^1$R$^2$(CR$^3$R$^4$)$_x$— and wherein Y is the bond location to the carbonyl carbon;

R$^1$, R$^2$, R$^3$ and R$^4$ are independently selected from the group consisting of hydrogen, halogen, substituted or unsubstituted alkyl of 1 to 25 carbons, substituted or unsubstituted aryl of 6 to 25 carbons, substituted or unsubstituted aralkyl of 7 to 26 carbons, substituted or unsubstituted alkoxy alkyl of 2 to 25 carbons, halogen-substituted alkyl of 1 to 25 carbons, substituted or unsubstituted alkoxy of 2 to 25 carbons, substituted or unsubstituted thioalkoxy of 1 to 25 carbons, dialkylamino of 2 to 25 carbons and diarylamino of 12 to 25 carbons, where the substituents for any of $R^1$, $R^2$, $R^3$ and $R^4$ are hydroxy, halogen, alkyl of 1 to 6 carbons or aryl of 6 to 12 carbons, with the proviso that $R^1$ and $R^3$ may together comprise a ring and $R^2$ and $R^4$ may together comprise a ring;

$R^5$, $R^6$, $R^7$, $R^8$, $R^9$ and $R^{10}$ are independently selected from the group consisting of hydrogen, halogen, substituted or unsubstituted alkyl of 1 to 25 carbons, substituted or unsubstituted aryl of 6 to 25 carbons, substituted or unsubstituted aralkyl of 7 to 26 carbons, substituted or unsubstituted alkoxy alkyl of 2 to 25 carbons, halogen-substituted alkyl of 1 to 25 carbons, substituted or unsubstituted alkoxy of 1 to 25 carbons, substituted or unsubstituted thioalkoxy of 1 to 25 carbons, dialkylamino of 2 to 25 carbons and diarylamino of 12 to 25 carbons, where the substituents for any of $R^5$, $R^6$, $R^7$, $R^8$, $R^9$ and $R^{10}$ are hydroxy, halogen, alkyl of 1 to 6 carbons or aryl of 6 to 12 carbons;

x is an integer from 2 to 5;
y is an integer from 1 to 5; and
Z is selected from the group consisting of —OH and —SR.

6. The process according to claim 5 wherein
R is substituted or unsubstituted aryl of 6 to 10 carbons;
$R^1$, $R^2$, $R^3$ and $R^4$ are independently selected from the group consisting of hydrogen and substituted or unsubstituted alkyl of 1 to 10 carbons; and
$R^5$, $R^6$, $R^7$, $R^8$, $R^9$ and $R^{10}$ are independently selected from the group consisting of hydrogen and substituted or unsubstituted alkyl of 1 to 10 carbons.

7. The process according to claim 5 wherein
R is substituted or unsubstituted alkyl of 1 to 10 carbons;
$R^1$, $R^2$, $R^3$ and $R^4$ are independently selected from the group consisting of hydrogen and substituted or unsubstituted alkyl of 1 to 10 carbons; and
$R^5$, $R^6$, $R^7$, $R^8$, $R^9$ and $R^{10}$ are independently selected from the group consisting of hydrogen and substituted or unsubstituted alkyl of 1 to 10 carbons.

8. The process according to claim 5 wherein
A comprises —$YCR^1R^2(CR^3R^4)_x$;
$R^1$, $R^2$, $R^3$ and $R^4$ are each hydrogen;
R is n-octyl;
Z is selected from the group consisting of hydroxy and n-octyl mercaptyl; and
x is 2.

9. The process according to claim 5 wherein the acidic catalyst is selected from the group consisting essentially of zeolites, silicalites, silica, silica-aluminas and methanesulfonic acid.

10. The process according to claim 5 wherein the temperature is about 150° C. to about 250° C.

11. The process according to claim 5 wherein the temperature is about 190° C. to about 250° C.

12. The process according to claim 5 further comprising
(a) introducing the lactone and mercaptan into a reactor containing the catalyst;
(b) heating the lactone and mercaptan to a temperature and for a time sufficient to produce a thio-substituted carboxylic acid and a thio-substituted thioester;
(c) introducing a mixture of the thio-substituted carboxylic acid, thio-substituted thioester, unreacted lactone and unreacted mercaptan into a first distillation column heated to a temperature and subjected to a pressure sufficient to cause the unreacted lactone and the unreacted mercaptan to recycle back into the reactor to form the thio-substituted carboxylic acid and the thio-substituted thioester; and
(d) removing the mixture comprising the thio-substituted carboxylic acid and thio-substituted thioester from the first distillation column.

13. The process according to claim 12 further comprising separating the thio-substituted carboxylic acid and thio-substituted thioester in a second distillation column.

14. The process of claim 12 wherein the reactor temperature is about 150° C. to about 250° C.

15. The process of claim 12 wherein the reactor temperature is about 190° C. to about 250° C.

16. The process of claim 13 wherein the temperature of the first and second distillation column is about 50° C. to about 250° C.

17. The process of claim 13 wherein the pressure of the first and second distillation column is about 5 millimeters of mercury to about 760 millimeters of mercury.

18. The process of claim 5 further comprising
(a) introducing the lactone and mercaptan into a reactor containing the catalyst;
(b) heating the lactone and mercaptan to a temperature and pressure and for a time sufficient to vaporize the lactone and mercaptan;
(c) introducing the vaporized lactone and mercaptan into a reflux column to produce a mixture predominantly of a thio-substituted carboxylic acid and a minor amount of a thio-substituted thioester;
(d) removing the mixture of the thio-substituted carboxylic acid and the thio-substituted thioester from the reflux column and reactor; and
(e) separating the thio-substituted carboxylic acid and the thio-substituted thioester from the mixture by distillation.

19. The process of claim 18 wherein the reactor temperature is about 150° C. to about 250° C.

20. The process of claim 18 wherein the reactor temperature is about 190° C. to about 250° C.

21. The process of claim 18 wherein the reactor pressure is about 5 millimeters of mercury to about 760 millimeters of mercury.

22. The process of claim 18 wherein the distillation column temperature is about 50° C. to about 250° C.

23. The process of claim 17 wherein the distillation pressure is about 5 millimeters of mercury to about 760 millimeters of mercury.

24. The process according to claim 5 further comprising
(a) introducing a batch of the lactone and mercaptan into a reactor containing about 0.1 to about 50 weight percent catalyst based on the weight of the lactone and mercaptan;
(b) heating the reaction batch while stirring and maintaining a pressure of about 10 psig to about 50 psig in the reactor for a time sufficient to produce a mixture of a thio-substituted carboxylic acid and a thio-substituted thioester;
(c) removing the mixture from the reactor; and (d) separating the thio-substituted carboxylic acid and the thio-substituted thioester from the mixture and from each other.

25. The process of claim 24 wherein the reactor temperature is about 150° C. to about 250° C.

26. The process of claim 24 wherein the reactor temperature is about 190° C. to about 250° C.

27. The process of claim 24 wherein the amount of catalyst is about 10% by weight based on the weight of mercaptan and lactone.

* * * * *